United States Patent [19]
Pietsch et al.

[11] 4,456,711
[45] Jun. 26, 1984

[54] PROCESS FOR THE PREPARATION OF A POWDER MIXTURE FOR SURGICAL USE

[75] Inventors: Hanns Pietsch, Hamburg; Volker Hohmann, Norderstedt; Willi Eckloff, Hamburg, all of Fed. Rep. of Germany

[73] Assignee: Beiersdorf Aktiengesellschaft, Hamburg, Fed. Rep. of Germany

[21] Appl. No.: 397,957

[22] Filed: Jul. 14, 1982

[30] Foreign Application Priority Data

Jul. 22, 1981 [DE] Fed. Rep. of Germany ....... 3128923

[51] Int. Cl.$^3$ .............................................. C08K 9/00
[52] U.S. Cl. .................................. 523/206; 524/431; 524/560; 523/205
[58] Field of Search ............... 523/206, 205, 431, 560

[56] References Cited

FOREIGN PATENT DOCUMENTS 1532318 11/1976 United Kingdom .

Primary Examiner—Joseph L. Schofer
Assistant Examiner—J. M. Reddick
Attorney, Agent, or Firm—Sprung, Horn, Kramer & Woods

[57] ABSTRACT

A powder mixture for surgical use, containing a methyl methacrylate homopolymer and/or copolymer powder, an X-ray contrast medium powder and a polymerization initiator, wherein the polymerization initiator is present as a combination product with the polymer powder or the X-ray contrast medium. This powder mixture is suitable for the preparation of surgical compositions which harden and are based on polymethyl methacrylate or its copolymers.

6 Claims, No Drawings

PROCESS FOR THE PREPARATION OF A POWDER MIXTURE FOR SURGICAL USE

The invention relates to a powder mixture for surgical compositions which harden and are based on polymethyl methacrylate, that is to say so-called bone cements.

Such compositions are preferably used for the implantation of joint prostheses, and most frequently for the implantation of hip joint prostheses. Other indications are compound osteosyntheses for spontaneous fractures and fractures of osteoporotic bones. Still further indications, such as replacement of parts of the skeleton and spinal column fusions, have been described in more detail in the book by O. Oest, K. Müller and W. Hupfauer; "Die Knochenzemente" ("Bone Cements"), F. Enke Verlag, Stuttgart 1975, pages 14–26.

These compositions are two-component systems which consist of a powder mixture and a liquid. The powder mixture consists of a polymer powder, preferably polymethyl methacrylate powder or pulverulent copolymers with methyl methacrylate units, X-ray contrast media, such as barium sulfate or zirconium dioxide, and the polymerization initiator, which is an organic peroxide, preferably dibenzoyl peroxide. The liquid phase consists chiefly of methyl methacrylate and/or other acrylates or methacrylates, and an accelerator, usually N,N-dimethyl-p-toluidine. Such bone cements are described in German Auslegeschrift No. 2,552,070.

After implantation, bone cements remain permanently in the human body. In many countries, they are equated with medicaments and are liable for registration at the State Health Offices. Accordingly, correspondingly high requirements are placed on the purity of the raw materials. This applies to all the constituents: polymer powder, X-ray contrast medium and polymerization initiator.

The polymerization initiator usually employed in bone cements is benzoyl peroxide. Benzoyl peroxide is flammable and explosive. For safety reasons, it may not be marketed or transported in the pure form.

For this reason, commercially available types of benzoyl peroxide are "desensitized", that is to say they are provided with concomitant non-explosive, non-flammable materials. Examples of such concomitant materials are water and plasticizers, such as dibutyl phthalate. Because of the purity requirements described, a polymerization initiator diluted with a plasticizer cannot be used as a constituent for bone cement. However, it would be conceivable to use water-moist benzoyl peroxide.

Because of their water content, such water-moist benzoyl peroxides are somewhat tacky, they agglomerate into loose aggregates and have poor flow characteristics. This means that powder mixtures prepared with these materials have a non-homogeneous distribution of peroxide: individual parts of a batch contain different amounts of peroxide and there are "pockets of peroxide" within one unit pack.

Both effects are undesirable. The first effect means that there is no uniform dosage of the peroxide and that individual packs from one preparation batch have different contents of peroxide. The second effect is also unpleasant and undesirable, and it leads to impairments of the hardened bone cement.

Although a mixing operation takes place during stirring of a bone cement when the powder phase is mixed with the liquid phase, this is frequently insufficient to compensate for inhomogeneities in the powder mixture, since, depending on the recipe, this mixing operation is effected within 2 to 5 minutes. On the contrary, it must be taken into account that in adverse cases the inhomogeneities are not compensated but cumulate.

The following adverse effects can then occur in the hardened bone cement: inhomogeneous distribution of strength, inhomogeneous distribution of heat during hardening, inhomogeneous distribution of residual monomer, and inhomogeneous distribution of residual peroxide, all of which can finally promote loosening of the prosthesis.

The object of the invention was to avoid the disadvantages described, in particular to ensure homogeneous distribution of the polymerization initiator in the powder mixture without additionally having to introduce foreign substances into the mixture. At the same time, safe handling of the initiator should be ensured, and the corresponding safety regulations should be taken into consideration.

According to the invention, this object is achieved by substantially improving the powder mixture in two-component systems of powder mixture and liquid, in particular by using the polymerization initiator not by itself but as a combination product with one of the other two characteristic constituents for such surgical compositions. The combination products used according to the invention thus consist of initiator on the one hand and polymerization powder or X-ray contrast medium on the other hand.

The build-up of the combination products or product is preferably such that the particles of polymer powder or X-ray contrast medium serve as carriers which are enveloped by the initiator. In one embodiment, the X-ray contrast medium zirconium dioxide serves as a carrier for a coating of benzoyl peroxide. The amount of peroxide can be between 1 and 50% by weight, and is preferably 2 to 25% by weight, especially 5–20% by weight. The amount of X-ray contrast medium is accordingly 99–50% by weight, preferably 98–75% by weight. Using these combination products, the powder mixtures according to German Auslegeschrift No. 2,552,070, for example, can be prepared in the proportions given therein, and, as described therein, can be reacted with a homogeneous water emulsion.

Such combination products can be prepared in a manner which is known per se, for example by a process in which the material to be coated is dried, with agitation, whilst the coating material is applied as a solution. The solvent for the coating material should not dissolve the material to be coated. Examples of such processes are fluidized bed drying or the preparation of coated tablets. Examples of suitable solvents are ethanol or ether for the coating of polymethyl methacrylate with benzoyl peroxide. Chlorinated hydrocarbons, such as methylene chloride, chloroform or carbon tetrachloride, are also suitable for the coating of an X-ray contrast medium with benzoyl peroxide.

Depending on the nature of the combination product, the powder mixtures according to the invention which are to be prepared with the aid of these combination products can, in particular, either (a) consist of the combination product and polymethyl methacrylate, if the combination product consists of an X-ray contrast medium and an initiator, or (b) consist of the combination product and an X-ray contrast medium, if the combination product consists of a polymer powder and an initiator.

The use of such a combination product gives homogeneous powder mixtures, the stationary state being achieved earlier than in the case when benzoyl peroxide desensitized with water is used. Surprisingly, it has additionally been found that, when a combination product with a polymerization initiator on the surface of powder particles is used, the effective surface of the initiator is greater than when the hitherto customary crystalline types, which in addition were also partly formed into lumps by water, are used. It is thus possible to accelerate the hardening reaction in the process according to the invention with the same peroxide content in the powder mixture, or to reduce the peroxide content with the same hardening rate. Since residual peroxide in the hardened bone cement is toxic, this is an improvement in the quality of the bone cement.

It has also been found that the diameter of the particles rises by at most about 20% as a result of the coating with the initiator. If, for example, the component with the smallest mean particle diameter is used as the carrier for the initiator, the maximum particle diameter is not exceeded.

It has been found that, using a maximum coating of 50%, the maximum particle diameter of 200 micrometers was not exceeded.

EXAMPLE 1

Comparison with the state of the art according to German Auslegeschrift No. 2,552,070.

Three powder mixtures each of 1 kg were prepared by mixing the following constituents: 882.5 g of polymethyl methacrylate powder, 100.0 g of zirconium dioxide powder and 17.5 g of 80% pure, water-moist dibenzoyl peroxide.

Each kg was mixed for 30 minutes, 60 minutes or 120 minutes in a twin-cone powder mixer and then divided into 50 g portions, each portion being subjected to two peroxide determinations by iodometric titration.

The results are summarized in Table 1.

The individual values were statistically processed and the standard deviation s, the arithmetic mean $\bar{x}$, the variation coefficient V and the relative variation coefficient $V_r$ were determined.

$$\bar{x} = \frac{\Sigma x_i}{n} \quad V = \frac{s}{\bar{x}}$$

$$s^2 = \frac{\Sigma(x_1 - \bar{x})^2}{n - 1} \quad V_r\% = \sqrt{\frac{\frac{s}{\bar{x}}}{n - 1}} \cdot 100$$

according to Lothar Sachs, Angewandte Statistik (Applied Statistics) and Erwin Kreyszig, Statistische Methoden und ihre Anwendung (Statistical Methods and their Application).

The percentage analytical error in the determination of peroxide was determined from all the values (comparison experiment and the example according to the invention, n=80) from the formula $$F\% = \frac{2 \cdot |x_1 - x_j|}{x_1 + x_j} \cdot 100$$

and has a relative value of 2.84%.

Batch 1 was mixed on a powder mixer for 30 minutes
Batch 2 was mixed on a powder mixer for 60 minutes
Batch 3 was mixed on a powder mixer for 120 minutes Each batch was divided into 20 samples of 50 g each, and the peroxide content of each sample was determined iodometrically, the results being listed in Table 1. It can be seen that 30 minutes is too short a mixing time, and that after 1 hour, a result is obtained which cannot be improved even after 2 hours. The inhomogeneity of the mixtures is seen from the relative variation coefficients, which drops from 10.2% after 30 minutes to 1.7% after 60 minutes and 120 minutes.

TABLE 1

| | Peroxide determination in the bone cement powder | | | | | | | | |
|---|---|---|---|---|---|---|---|---|---|
| | 30 minutes mixing time benzoyl peroxide | | | 60 minutes mixing time | | | 120 minutes mixing time | | |
| Number | I | II | Δ | I | II | Δ | I | II | Δ |
| 1 | 1.21 | 1.27 | 0.06 | 1.31 | 1.27 | 0.04 | 1.33 | 1.35 | 0.02 |
| 2 | 1.20 | 1.35 | 0.15 | 1.32 | 1.30 | 0.02 | 1.53 | 1.55 | 0.02 |
| 3 | 1.38 | 1.34 | 0.04 | 1.32 | 1.31 | 0.01 | 1.52 | 1.48 | 0.04 |
| 4 | 1.10 | 1.18 | 0.08 | 1.52 | 1.54 | 0.02 | 1.47 | 1.44 | 0.07 |
| 5 | 1.24 | 1.23 | 0.01 | 1.45 | 1.37 | 0.08 | 1.42 | 1.45 | 0.03 |
| 6 | 1.40 | 1.30 | 0.10 | 1.31 | 1.29 | 0.02 | 1.31 | 1.34 | 0.03 |
| 7 | 1.28 | 1.33 | 0.05 | 1.36 | 1.33 | 0.03 | 1.42 | 1.46 | 0.04 |
| 8 | 1.21 | 1.15 | 0.06 | 1.21 | 1.29 | 0.08 | 1.24 | 1.27 | 0.03 |
| 9 | 1.23 | 1.20 | 0.03 | 1.53 | 1.48 | 0.05 | 1.45 | 1.42 | 0.03 |
| 10 | 1.35 | 1.36 | 0.01 | 1.56 | 1.49 | 0.07 | 1.55 | 1.53 | 0.02 |
| 11 | 1.13 | 1.20 | 0.07 | 1.51 | 1.53 | 0.02 | 1.37 | 1.37 | 0.01 |
| 12 | 1.35 | 1.31 | 0.04 | 1.40 | 1.46 | 0.06 | 1.60 | 1.67 | 0.07 |
| 13 | 1.12 | 1.15 | 0.03 | 1.52 | 1.53 | 0.01 | 1.40 | 1.47 | 0.07 |
| 14 | 1.31 | 1.28 | 0.03 | 1.45 | 1.48 | 0.03 | 1.34 | 1.37 | 0.03 |
| 15 | 1.29 | 1.21 | 0.08 | 1.41 | 1.49 | 0.08 | 1.31 | 1.34 | 0.03 |
| 16 | 1.18 | 1.11 | 0.07 | 1.35 | 1.34 | 0.01 | 1.49 | 1.45 | 0.04 |
| 17 | 1.26 | 1.33 | 0.07 | 1.48 | 1.42 | 0.06 | 1.33 | 1.35 | 0.02 |
| 18 | 1.51 | 1.50 | 0.01 | 1.49 | 1.50 | 0.01 | 1.49 | 1.44 | 0.05 |
| 19 | 4.00 | 4.02 | 0.02 | 1.29 | 1.30 | 0.01 | 1.53 | 1.51 | 0.02 |
| 20 | 1.22 | 1.20 | 0.02 | 1.43 | 1.42 | 0.01 | 1.25 | 1.24 | 0.01 |
| $\bar{x}$ | 1.37 | 1.38 | | 1.41 | 1.407 | | 1.418 | 1.425 | |
| s | 0.6 | 0.3 | | ±0.098 | ±0.096 | | 0.105 | 0.100 | |
| n | 20 | 20 | | 20 | 20 | | 20 | 20 | |
| V | 0.444 | 0.445 | | 0.070 | 0.068 | | 0.074 | 0.071 | |

TABLE 1-continued

| | Peroxide determination in the bone cement powder | | | | | | | | |
|---|---|---|---|---|---|---|---|---|---|
| | 30 minutes mixing time benzoyl peroxide | | | 60 minutes mixing time | | | 120 minutes mixing time | | |
| Number | I | II | Δ | I | II | Δ | I | II | Δ |
| $V_r$ (%) | 10.2 | 10.2 | | 1.6 | 1.6 | | 1.7 | 1.6 | |

Example 2 (according to the invention)

886 g of polymethyl methacrylate powder, 100 g of a combination product of 86% by weight of zirconium dioxide powder and 14% by weight of benzoyl peroxide and 14 g of zirconium dioxide powder were mixed in a powder mixer for one hour as in Example 1, and the peroxide content of the mixture was then determined iodometrically:

TABLE 2

| | Results Peroxide content of the sample: | | |
|---|---|---|---|
| | I | II | Δ |
| 1 | 1.40 | 1.43 | 0.03 |
| 2 | 1.43 | 1.41 | 0.02 |
| 3 | 1.35 | 1.40 | 0.05 |
| 4 | 1.44 | 1.44 | 0.05 |
| 5 | 1.45 | 1.41 | 0.04 |
| 6 | 1.35 | 1.38 | 0.03 |
| 7 | 1.38 | 1.35 | 0.03 |
| 8 | 1.41 | 1.44 | 0.03 |
| 9 | 1.41 | 1.44 | 0.03 |
| 10 | 1.40 | 1.38 | 0.02 |
| 11 | 1.44 | 1.40 | 0.04 |
| 12 | 1.40 | 1.36 | 0.04 |
| 13 | 1.38 | 1.35 | 0.03 |
| 14 | 1.38 | 1.39 | 0.01 |
| 15 | 1.46 | 1.41 | 0.05 |
| 16 | 1.35 | 1.39 | 0.04 |
| 17 | 1.39 | 1.45 | 0.06 |
| 18 | 1.49 | 1.41 | 0.08 |
| 19 | 1.38 | 1.40 | 0.02 |
| 20 | 1.41 | 1.46 | 0.05 |
| n | 20 | 20 | |
| x | 1.405 | 1.406 | |
| s | 0.038 | 0.033 | |
| V | 0.027 | 0.023 | |
| $V_r$(%) | 0.6 | 0.5 | |

In the mixture according to the invention, a mixture with $V_r$=0.5 is obtained within one hour, which is a homogeneity three times better than that achieved according to Example 1 (state of the art).

Example 3 (according to the invention)

As described in Example 1, but using a combination product of 85% of polymethyl methacrylate and 15% of benzoyl peroxide:

803.2 g of polymethyl methacrylate powder, 100.0 g of zirconium dioxide powder and 93.3 g of a combination product of 85% by weight of polymethyl methacrylate and 15% by weight of benzoyl peroxide were mixed in a powder mixer for one hour, the mixture was divided into individual samples each of 50 g and the peroxide content of these samples was determined iodometrically. The theoretical peroxide content is 1.404%.

The following peroxide contents were measured (Table 3):

TABLE 3

| Number | Peroxide content Measurement 1 | Peroxide content Measurement 2 | Difference between Measurements 1 and 2 |
|---|---|---|---|
| 1 | 1.39 | 1.35 | 0.04 |
| 2 | 1.37 | 1.36 | 0.01 |
| 3 | 1.37 | 1.40 | 0.03 |
| 4 | 1.47 | 1.40 | 0.07 |
| 5 | 1.36 | 1.38 | 0.02 |
| 6 | 1.38 | 1.44 | 0.06 |
| 7 | 1.48 | 1.40 | 0.08 |
| 8 | 1.39 | 1.41 | 0.02 |
| 9 | 1.42 | 1.45 | 0.03 |
| 10 | 1.41 | 1.44 | 0.03 |
| 11 | 1.44 | 1.42 | 0.02 |
| 12 | 1.34 | 1.39 | 0.05 |
| 13 | 1.43 | 1.43 | 0.00 |
| 14 | 1.46 | 1.40 | 0.06 |
| 15 | 1.36 | 1.37 | 0.01 |
| 16 | 1.37 | 1.36 | 0.01 |
| 17 | 1.40 | 1.45 | 0.05 |
| 18 | 1.40 | 1.43 | 0.03 |
| 19 | 1.41 | 1.31 | 0.02 |
| 20 | 1.45 | 1.41 | 0.04 |
| n | 20 | 20 | 20 |
| x | 1.405 | 1.405 | 0.034 |
| s | 0.034 | 0.032 | |
| V | 0.024 | 0.022 | |
| $V_r$(%) | 0.55 | 0.505 | |

In this case also, a mixture is obtained which has a homogeneity which is improved three-fold compared with the state of the art (V-% in Example 3: 0.55 and 0.505, compared with 1.6 in Example 1, which represents the state of the art).

We claim:

1. In a process for the preparation of a powder mixture which comprises combining a polymerization initiator with a methylmethacrylate homopolymer and/or copolymer powder and an X-ray contrast medium, the improvement wherein the initiator is mixed with either the polymer powder or the X-ray contrast medium under conditions whereby the initiator coats said polymer powder or said X-ray contrast medium and, subsequently mixing the remainder of the ingredients".

2. A process as in claim 1, wherein the X-ray contrast medium is zirconium dioxide powder which is coated with benzoyl peroxide as the initiator.

3. A process as in claim 1, wherein the polymer powder is coated with benzoyl peroxide.

4. A process as in claim 1, wherein the content of the initiator is 1–50% by weight.

5. A process as in claim 1, wherein the content of X-ray contrast medium is up to 15% by weight.

6. A process as in claim 1, wherein the maximum particle diameter of said mixture is less than 200 micrometers.

* * * * *